(12) United States Patent
Johnson (10) Patent No.: US 9,155,646 B2
(45) Date of Patent: Oct. 13, 2015

(54) COMPOSITE STENT WITH BIOREMOVABLE CERAMIC FLAKES

(75) Inventor: James R. Johnson, Lady Lake, FL (US)

(73) Assignee: BRS Holdings, LLC, Rosemount, MN (US)

( * ) Notice: Subject to any disclaimer, the term of this patent is extended or adjusted under 35 U.S.C. 154(b) by 1270 days.

(21) Appl. No.: 11/380,572

(22) Filed: Apr. 27, 2006

(65) Prior Publication Data

US 2007/0255392 A1 Nov. 1, 2007

(51) Int. Cl.
| A61F 2/06 | (2013.01) |
| A61F 2/92 | (2013.01) |
| A61L 31/08 | (2006.01) |
| A61L 31/12 | (2006.01) |
| A61L 31/14 | (2006.01) |

(52) U.S. Cl.
CPC ............... *A61F 2/92* (2013.01); *A61L 31/086* (2013.01); *A61L 31/126* (2013.01); *A61L 31/148* (2013.01); *A61F 2210/0076* (2013.01)

(58) Field of Classification Search
USPC .............. 623/1.15, 1.34, 1.44, 1.49, 1.13; 606/191, 192, 194, 198; 604/103.1, 604/362, 529
See application file for complete search history.

(56) References Cited

U.S. PATENT DOCUMENTS

| 3,436,307 | A | 4/1969 | Johnson et al. |
| 3,444,929 | A | 5/1969 | Brown et al. |
| 3,709,706 | A | 1/1973 | Sowman |
| RE27,747 | E | 9/1973 | Johnson |
| 3,795,524 | A | 3/1974 | Sowman |
| 3,832,457 | A * | 8/1974 | Sugimoto et al. ......... 424/9.411 |
| 4,166,147 | A | 8/1979 | Lange et al. |
| 4,649,920 | A | 3/1987 | Rhum |
| 4,801,562 | A | 1/1989 | Sowman et al. |
| 5,084,051 | A * | 1/1992 | Tormala et al. ............... 606/77 |
| 5,629,077 | A | 5/1997 | Turnlund et al. |
| 5,665,120 | A * | 9/1997 | Ohtsuka et al. ............. 424/423 |
| 5,728,150 | A | 3/1998 | McDonald et al. |
| 5,958,314 | A * | 9/1999 | Draenert ......................... 264/42 |
| 5,980,564 | A | 11/1999 | Stinson |
| 6,136,029 | A | 10/2000 | Johnson et al. |
| 6,296,667 | B1 | 10/2001 | Johnson et al. |
| 6,325,822 | B1 | 12/2001 | Chouinard et al. |
| 6,338,739 | B1 | 1/2002 | Datta et al. |

(Continued)

FOREIGN PATENT DOCUMENTS

| EP | 1 639 962 A2 | 12/2000 |
| EP | 1 721 625 A2 | 2/2006 |

(Continued)

OTHER PUBLICATIONS

"Implantable Elution Devices: Reshaping the Industry," devicelink.com/mddi, MD & DI, Jul. 2005, pp. 54-55.

(Continued)

*Primary Examiner* — Brian Pellegrino
(74) *Attorney, Agent, or Firm* — Brian E. Szymanski (57) ABSTRACT

A biodegradable and/or bioabsorbable composite stent includes a bioabsorbable ceramic material dispersed and embedded in a biodegradable polymeric material. The bioabsorbable ceramic material is made of flakes that have a thin, flat shape. In one embodiment, the composite stent comprises a body of one or more layers of polymer alone coupled to layers of polymer in which the ceramic flakes are dispersed and embedded and the composite is coiled to form the stent.

35 Claims, 4 Drawing Sheets

(56) References Cited

U.S. PATENT DOCUMENTS

| | | |
|---|---|---|
| 6,368,703 B1 | 4/2002 | Johnson |
| 6,409,750 B1 | 6/2002 | Hyodoh et al. |
| 6,527,810 B2 | 3/2003 | Johnson et al. |
| RE38,158 E | 6/2003 | Barrows et al. |
| 6,605,648 B1 | 8/2003 | Johnson et al. |
| 6,623,521 B2 | 9/2003 | Steinke et al. |
| 6,626,936 B2 | 9/2003 | Stinson |
| 6,641,609 B2 | 11/2003 | Globerman |
| 6,652,575 B2 | 11/2003 | Wang |
| 6,656,218 B1 | 12/2003 | Denardo et al. |
| 6,656,587 B2 | 12/2003 | Johnson et al. |
| 6,719,934 B2 | 4/2004 | Stinson |
| 6,747,121 B2 | 6/2004 | Gogolewski |
| 6,749,629 B1 | 6/2004 | Hong et al. |
| 6,805,705 B2 | 10/2004 | Hong et al. |
| 6,814,750 B2 | 11/2004 | Kavteladze et al. |
| 6,849,186 B2 | 2/2005 | Johnson et al. |
| 6,854,172 B2 | 2/2005 | Kaese et al. |
| 6,869,445 B1 | 3/2005 | Johnson |
| 6,890,350 B1 | 5/2005 | Walak |
| 6,913,619 B2 | 7/2005 | Brown et al. |
| 6,913,762 B2 | 7/2005 | Caplice et al. |
| 6,929,626 B2 | 8/2005 | DiCarlo et al. |
| 6,972,130 B1 | 12/2005 | Lee et al. |
| 6,977,095 B1 | 12/2005 | Marx et al. |
| 6,984,671 B2 | 1/2006 | Johnson et al. |
| 6,991,647 B2 | 1/2006 | Jadhav |
| 6,993,406 B1 | 1/2006 | Cesarano, III et al. |
| 6,997,948 B2 | 2/2006 | Stinson |
| 7,108,716 B2 | 9/2006 | Burnside et al. |
| 7,744,644 B2 * | 6/2010 | Weber et al. ............ 623/1.42 |
| 2002/0103527 A1 | 8/2002 | Kocur et al. |
| 2002/0165523 A1 * | 11/2002 | Chin et al. ............... 604/523 |
| 2005/0163954 A1 * | 7/2005 | Shaw ..................... 623/1.15 |
| 2005/0239628 A1 | 10/2005 | Johnson et al. |
| 2006/0045901 A1 | 3/2006 | Weber |
| 2006/0199876 A1 | 9/2006 | Troczynski et al. |
| 2006/0264531 A1 | 11/2006 | Zhao |
| 2007/0207186 A1 | 9/2007 | Scanlon et al. |

FOREIGN PATENT DOCUMENTS

| | | | |
|---|---|---|---|
| EP | 1 634 609 A2 | 3/2006 | |
| WO | WO 9818408 A1 * | 5/1998 | ............ A61F 2/06 |
| WO | WO 02/060337 A2 | 8/2002 | |
| WO | WO 03/068288 A1 | 8/2003 | |
| WO | WO 2004/024201 A2 | 3/2004 | |
| WO | WO 2004092430 A2 * | 10/2004 | ............ B32B 15/04 |
| WO | WO 2006/014969 A2 | 2/2006 | |

OTHER PUBLICATIONS

Kling, Jim, "Elution, Boston Scientific's blockbuster medical device—and the novel way it was developed," printed from website www.technologyreview.com on Apr. 27, 2006, 3 pages.

"MIV Therapeutics' HAp Nano Stent Coating Demonstrates Excellent Biocompatibility," Archived Nanotechnology News, Posted Mar. 10, 2005, 2 pages.

Smock, Doug, "Medical Miracles," Design News, Aug. 15, 2005, vol. 7, 9 pages.

International Search Report and Written Opinion, PCT Application No. PCT/US07/67546, Nov. 8, 2007 (17 pages).

Di Mario, Carlo, M.D., et al., Drug-Eluting Bioabsorbable Magnesium Stent, *Journal of Interventional Cardiology*, vol. 17, No. 6, 2004, pp. 391-395 (5 pages).

Eberhart, Robert C., et al., Bioresorbable Polymeric Stents: Current Status and Future Promise, *J. Biomater.: Sci. Polymer Edn.* vol. 14, No. 4, 2003, pp. 299-312 (14 pages).

Alumina-reinforced polymer has high strength, flexibility, *Advanced Materials & Processes*, May 2008, p. 17 (1 page).

International Search Report and Written Opinion, obtained from related International Application No. PCT/US2008/082114, May 19, 2009 (16 pgs.).

Invitation to Pay Additional Fees and Communication Relating to the Results of the Partial International Search, obtained from related International Patent Application No. PCT/US2008/082114, Mar. 6, 2009 (6 pages).

\* cited by examiner

COMPOSITE STENT WITH BIOREMOVABLE CERAMIC FLAKES

BACKGROUND

Stents can generally be thought of as medical devices that support or keep open vessels, ducts, or other lumens in the body. Many stents are used to relieve an occlusion in blood vessels such as coronary arteries, veins, etc. However, stents may also be used in the intestines, the esophagus, urethra, biliary ducts, and the like.

In vascular stents, the stent is often designed to be flexible to allow the stent to be inserted into the vascular system and guided to the appropriate location. Typically, this is done using suitable guide wires, catheters, and the like. Once in position, the stent is designed to be opened and held in position in order to facilitate unobstructed flow through the vessel. Stents may be opened in a number of ways such as using a balloon catheter. The need for flexibility may vary according to the application within the body.

Stents that are left in place over a long period of time may cause problems. For example, the stent may cause weakening of the vessel wall which may result in formation of a thrombus, aneurysm, or the like. In addition, endothelial tissue may cover the stent and/or prevent treatment of restenosis. Accordingly, it would be desirable to provide a composite stent that is bioabsorbable and/or biodegradable to reduce the risk that is otherwise associated with permanent stents.

DETAILED DESCRIPTION

Although the subject matter described herein is provided in the context of stents generally, it should be appreciated that certain embodiments may be more suitable for a particular application than other embodiments. For example the stent shown in FIG. 1 may be more suited for intravascular use than for use in other vessels. Also, the stent shown in FIG. 5 may be more suited for use in the intestines or in other relatively larger lumens. That being said, it should be appreciated that any of the stents described herein may be used in any suitable lumen in the body. Also, it should be appreciated, that the features, advantages, characteristics, etc. of one embodiment may be applied to any other embodiment to form an additional embodiment unless noted otherwise.

Figure 1:
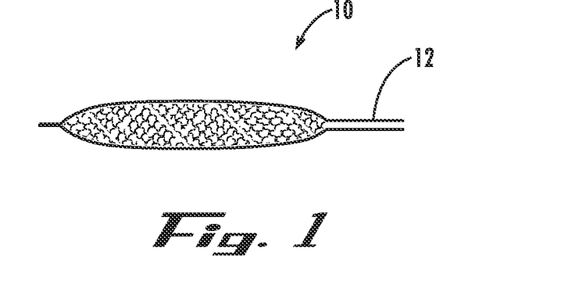
FIG. 1 shows a side view of a composite stent in a contracted configuration to allow the stent to be inserted into a lumen.

Referring to FIG. 1, a composite stent 10 is shown in a first configuration where the diameter or size of the stent 10 is reduced to allow the stent 10 to be inserted into a lumen. The stent 10 may be formed from a loose woven network of ceramic fibrous material. The stent 10 has a generally cylindrical or tubular shape that is configured to fit within a lumen. The stent 10 is composed to be bioremovable to allow the stent 10 to be safely and effectively removed over time from the vessel. It should be appreciated that the term "bioremovable" is used herein to refer to biocompatible materials that are capable of being broken down, gradually absorbed, and/or otherwise used by or eliminated from the body by processes such as bioabsorbtion (i.e., they are absorbed by the body and moved within the body to be used), biodegradation (i.e., chemically fall apart into non-toxic components that are carried away by material moving through the vessel), and the like. Thus, the term "bioremovable" is intended to encompass both bioabsorbtion and biodegradation processes.

Figure 2:
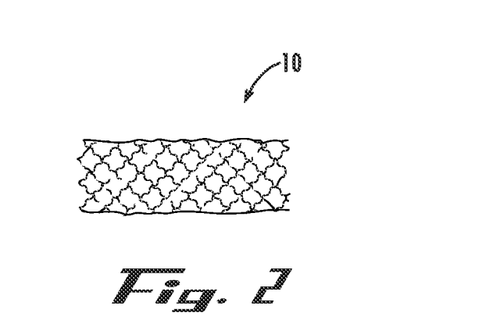
FIG. 2 shows a side view of the composite stent of FIG. 1 in an expanded configuration to thereby hold a lumen open.

In order to facilitate insertion into the lumen, the stent 10 may be releasably coupled to a catheter or guide wire 12. The catheter 12 is configured to allow the catheter 12 and stent 10 to pass through the lumen to the occluded site. Once the stent 10 is in position, the stent 10 can be expanded to open the occluded vessel and hold it open. In one embodiment, as the stent 10 is expanded, it may become shorter and larger in diameter. The stent 10 is shown in an expanded configuration in FIG. 2. The catheter 12 may then be withdrawn from the lumen leaving the stent 10 in place.

It should be noted that for purposes of this disclosure, the term "coupled" means the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature.

It should be appreciated that numerous methods may be used to expand the stent 10. In one embodiment, the catheter 12 may be a balloon catheter having a balloon positioned between the stent 10 and the main body of the catheter 12. The balloon can be inflated using a fluid such as saline solution. As the balloon is inflated, the stent 10 expands outward radially until the stent 10 is positioned to hold the lumen open. In general, the stent 10 is configured to expand in a lumen without substantial rotational movement relative to the longitudinal axis of the stent 10 (see stent 30 for an example where the stent expands by rotating about the longitudinal axis of the stent 30).

Figure 3:
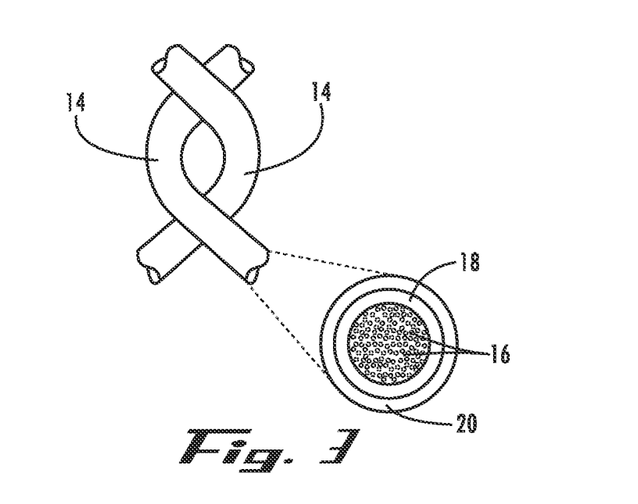
FIG. 3 shows a perspective and cross-sectional view of one embodiment of a composite yarn or fiber that may be used to form at least a part of the composite stent of FIG. 1.

It should be appreciated that any suitable bioremovable fibrous material may be used to form the stent 10 (e.g., inorganic fibrous material). Referring to FIG. 3, the fibrous material may include a loose network of composite yarns or composite fibers 14. The composite yarns 14 may be woven together in a loose weave such as that shown in FIG. 3, or the composite yarns 14 may be assembled in other ways besides weaving (e.g., using a suitable rubbery biodegradable polymer to engage the fibers to resist the movement of the fibers so as to enhance the structural integrity of the composite). It should be appreciated that the composite yarns 14 may be assembled together in a manner that allows the composite yarns 14 to expand so that the stent 10 can likewise expand to fill the lumen. At the same time, the composite yarns 14 should be configured so that upon expansion of the stent 10, the stent 10 has sufficient strength to remain in position in the lumen and keep the occluded site open.

FIG. 3 also shows a cross-sectional view of one of the composite yarns 14. Each composite yarn 14 includes a plurality of ceramic fibers 16 encased in or coated with a first or inner polymer layer or coating 18 which is in turn coated with a second or outer polymer layer or coating 20. It should be appreciated that the ceramic fibers 16 may be soaked with the first polymer coating 18 to completely fill in the interstices between the ceramic fibers 16, or the ceramic fibers 16 may be individually coated with the first polymer coating 18. The first polymer coating 18 may be provided to give resiliency and toughness to the composite yarn 14 by distributing the load on the ceramic fibers. The second polymer coating 20, a more rubbery bioremovable polymer than the first polymer coating 18, may engage the fibers 16/yarn 14 to make firm the structural integrity of the expanded stent 10. Thus, the first polymer coating 18 may have a different modulus of elasticity than the second polymer coating 20. In one embodiment, the first polymer coating 18 has a higher modulus of elasticity than the second polymer coating 20. Also, the first polymer coating 18 may have a different molecular weight than the second polymer coating 20. In one embodiment, the first polymer coating 18 may have a lower molecular weight than the second polymer coating 20.

The higher friction property of the second polymer coating 20 acts to hold the composite yarns 14 in the expanded state by friction forces and prevent the stent 10 from collapsing. It should be appreciated that the composite yarns 14 may include more than one polymer coating 18, 20. For example, the composite yarns 14 may be prepared by forming multiple resilient coatings over the ceramic fibers 16 with the final coating being a low modulus coating. The thickness of the first polymer coating 18 and the second polymer coating 20 may be about 0.1 to 5 microns.

It should be appreciated that in other embodiments of the stent 10 a single polymer coating may be used or more than one polymer coatings (e.g., three or more) may be used. For example, a single polymer coating may suffice so long as the polymer coating has the requisite stiffness to support the integrity of the stent 10 and the friction properties sufficient to hold the stent 10 in the expanded position. Also, bodily fluids (e.g., blood, etc.) may soften the surface of the polymer so that the polymer provides sufficient friction to hold the stent 10 open.

The stent 10 may be configured so that it gradually and uniformly erodes in the lumen (e.g., in the bloodstream of a patient) rather than eroding by periodically cleaving off large chunks. In one embodiment, each layer may be selected to provide protection against non-uniform erosion of the layer beneath it. The materials used in the stent 10 may be selected to provide sufficient support for the lumen at all times as the stent 10 is replaced by natural tissues.

The first polymer coating 18 and the second polymer coating 20 for the stent 10 may include bioremovable/biocompatible polymers. That is, the polymers will be removed by in-vivo processes such that the polymers and their products are not toxic or inhibit the purpose of the stent 10 and the products will be either eliminated from the body or assimilated by the body. Suitable examples of such polymers may be found among polyesters, polyols, polycarbonates, polyamides, polyethers, polysaccharides, and/or polyhydroxyalkanoates. Preferred examples include polylactide (PLA), polyglycolide (PGA), polycaprolactones, albumin, collagen, and/or mixtures thereof. PLA is used to refer to poly-L-lactide (PLLA) and/or poly-DL-lactide (PDLLA). In one embodiment, the first polymer coating 18 and the second polymer coating 20 each includes PLA and/or PGA.

The first polymer coating 18 is intended to provide a protective load-distributing layer on the ceramic fibers to inhibit fracture when the fibers are moved on expanding the stent 10. It may also have additional advantages such as modulating the rate of bioremoval processes and providing some intersurface friction between fibers. The polymer should have sufficient molecular entanglement to provide some toughness as well as the above features. For PLA for example, a molecular weight of about 20,000 to 150,000 daltons may be preferred.

The second polymer coating 20 is designed to have a glass transition temperature below body temperature. Its function is to further stabilize the open stent from retracting by increased friction, fiber on fiber, yarn on yarn, akin to locking the fibers in place. For example, the second polymer coating 20 may be a bioremovable polymer or copolymer of albumin having a modulus of less than $1\times10^7$ pascals. Further it is contemplated if necessary that the weave of the yarn that forms the stent 10 be such that when open, it provides some mechanical resistance to retracting.

Figure 4:
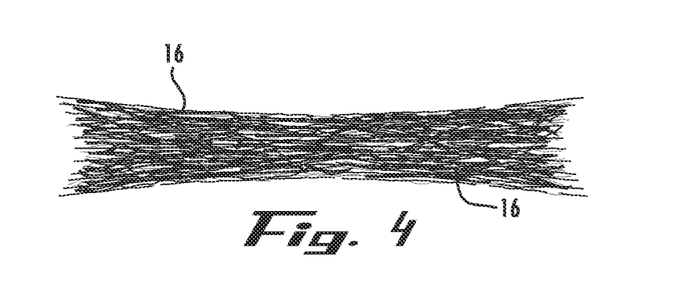
FIG. 4 shows a side view of a plurality of ceramic fibers which may be used in the composite yarn of FIG. 3.

FIG. 4 shows the ceramic fibers 16 prior to being coated with the first polymer coating 18. The ceramic fibers 16 are generally positioned parallel to each other prior to being coated with the first polymer coating 18. The ceramic fibers 16 may be any suitable size. In one embodiment, the ceramic fibers 16 may be about 0.5 microns to 10 microns in diameter or may be about 1 micron to 5 microns in diameter.

The ceramic fibers 16 may be made of any suitable bioremovable ceramic material(s). In one embodiment, the ceramic fibers 16 may include bioremovable ceramic material. Suitable examples of bioremovable ceramic material include calcium phosphate material such as tricalcium phosphate and/or other similar materials. In one embodiment, the calcium phosphate material may be bioabsorbable (i.e., incorporated into the body) rather than being biodegradable (i.e., removed by the body). Tricalcium phosphate is one example of a bioabsorbable material. In one embodiment, the bioremovable ceramic material may be substantially entirely made up of tricalcium phosphate. It should be appreciated that in other embodiments, the bioremovable ceramic material may include a mixture of tricalcium phosphate and another bioremovable ceramic material or may be made up entirely of bioremovable ceramic materials other than tricalcium phosphate. In another embodiment, the bioremovable ceramic material may be calcium phosphate material that has been fired to a temperature that makes them strong enough to endure the bending movements which occur during emplacement.

Additional bioremovable ceramic materials include bioactive glasses such as BIOGLASS as well as other similar materials. Unlike tricalcium phosphate, bioglass typically biodegrades and exits the body. In one embodiment, each composite yarn 14 may include multiple different types of bioremovable ceramic fibers 16. For example, the composite yarn 14 may include a mixture of bioactive glass fibers, tricalcium phosphate fibers, and/or other bioremovable ceramic fibers.

The ceramic fibers 16, for example, if they are to be beta tricalcium phosphate, may be prepared using a sol gel process as described in U.S. Pat. Nos. 3,795,524, 4,801,562, 4,929, 578, all of which are incorporated by reference herein in their entireties. In general, the process includes incorporating a source of calcium (e.g., calcium acetate, calcium formamide, other organic and inorganic compounds of calcium) that when mixed with a phosphorous source (e.g., phosphoric acid, phosphorous pentoxide) yield calcium phosphate. The purity of these materials are expected to meet ASTM F1088-04a specifications for implantable products. The salts are made in aqueous solutions and concentrated in a rotovapor device. The viscosity may be increased to about 200 to 1000 poises by adding glucose, corn syrup, or polyvinyl pyrrolidone (PVP) up to or more than ⅔ of the total volume. Since fibers are being made, the viscous material is drawn through a spinerette (a description of how to make flakes is described below). The resulting fibers are fired at temperatures up to about 1150° C.

The composite yarn 14 may have any suitable size depending on the application. The diameter of the composite yarn 14 depends on the number of ceramic fibers 16 used in the composite yarn 14. In one embodiment, each composite yarn 14 is about 20 microns to 150 microns in diameter or 50 microns to 100 microns in diameter. The rate that the bioremovable inorganic ceramic in the stent 10 disappears may be controlled by altering the porosity, thickness, and compositions of the materials being used. The ratio of the amount of PLA/PGA in a particular polymer coating may be altered to change the rate at which the polymer coating degrades around the composite yarn 14 within the other requirements for the coating. The ratio of PLA/PGA may be determined for each application to provide the desired degradation rate. Also, other biocompatible chemicals such as plasticizers may be used to control the rate of disappearance.

Figure 5:
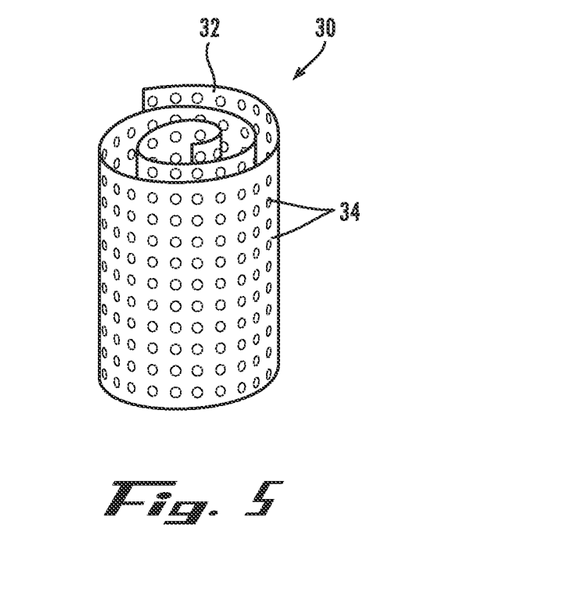
FIG. 5 shows a perspective view of another embodiment of a composite stent in a contracted configuration to allow the stent to be inserted into a lumen.

Referring to FIG. 5, another embodiment of a composite stent 30 is shown. In this embodiment, the stent 30 includes a sheet 32 having a plurality of holes or openings 34 in it. The stent 30 shown in FIG. 5 is wound or coiled so that it can be inserted into a lumen. Since the stent 30 is not as flexible as the stent 10, the stent 30 is typically more useful in larger vessels such as the intestines or in situations where the stent 30 implanted directly (often temporarily) into the vessel without passing it through long sections of curved vessel. The stent 30 may be expanded in any suitable manner such as, for example, using a balloon.

Figure 6:
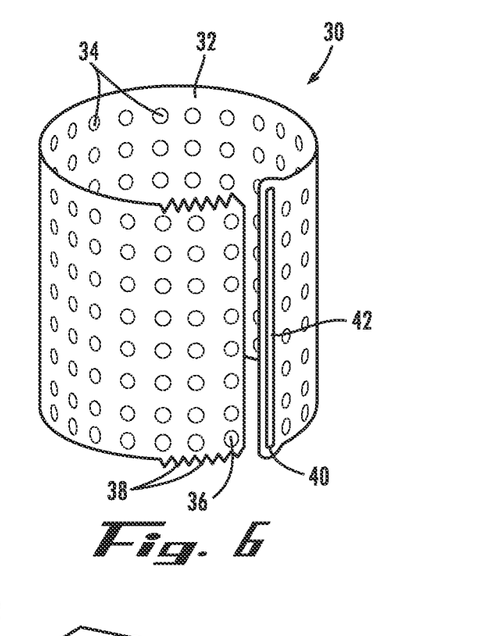
FIG. 6 shows a perspective view of one embodiment of the composite stent from FIG. 5 in an expanded configuration.

As shown in FIG. 6, the stent 30 may be held in the expanded position using a belt and buckle type configuration. The sheet 36 includes a first end 36 which has a plurality of teeth 38 thereon and a second end 40 which includes a buckle shaped opening 42 which is sized to receive the first end 36. When the stent 30 is in the expanded configuration, the teeth 38 engage the top and bottom of the opening 42 to prevent the stent 30 from collapsing. The use of the belt and buckle type configuration allows the stent 30 be mechanically locked in position. It is also contemplated that the stent 30 may be held open due to the adhesiveness from a low modulus bioremovable polymer coating, for example. The stent 30 may also be held open using a mechanical fastener system such as a slot insert system.

Figure 7:
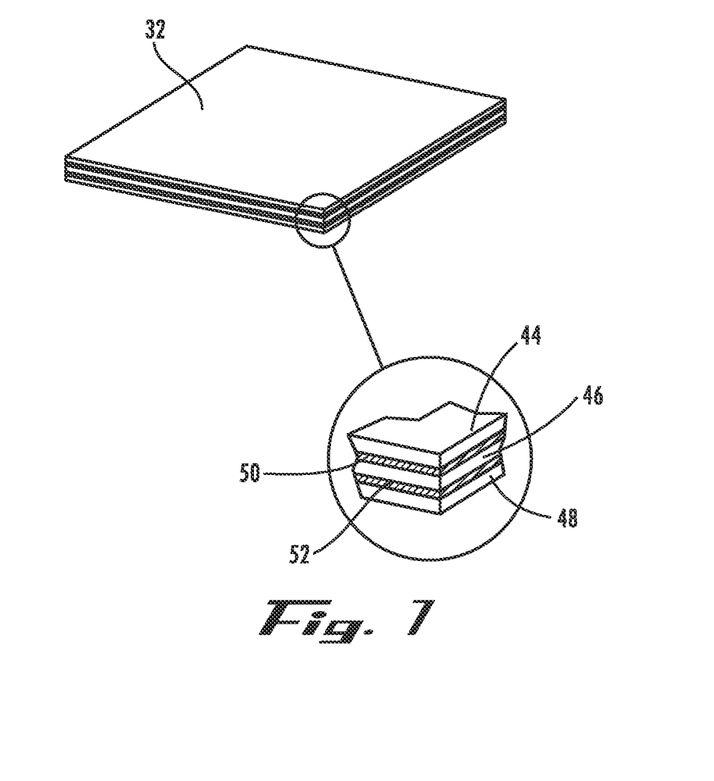
FIG. 7 shows a perspective view of a sheet of material that may be used to form at least part of the composite stent from FIG. 5.

The stent 30 may include a plurality of layers of different materials as shown in FIG. 7. In one embodiment, the stent 30 may include alternating layers of ceramic material and polymeric material. The stent 30 may include at least two layers of material, or suitably, at least three layers of material and may go up to no more than twenty one layers of material or no more than fifteen layers of material. The layers of material may be coupled together to form a relatively resilient structure where the polymer provides this feature by distributing the load on bending of the stent. In one embodiment, the thickness of the sheet 32 may be about 10 to 200 microns, desirably about 30 to 150 microns, or suitably 40 to 100 microns.

The material used to form the sheet 32 may be bioremovable. For example, the sheet 32 may include alternating layers of bioremovable polymer and bioremovable ceramic material. In one embodiment, the outer two layers of the sheet 32 may be bioremovable polymer layers. Thus, the bioremovable ceramic material layers are on the inside of the sheet 32. In another embodiment, the outer two layers of the sheet 32 may include bioremovable ceramic material. In this configuration the bioremovable polymer layers may be on the inside of the sheet 32. Each layer of bioremovable ceramic material may be about 1 to 20 microns thick or about 2 to 10 microns thick. Each layer of the bioremovable polymer may be about 0.1 to 10 microns thick, 0.5 to 8 microns thick, or 1 to 5 microns thick. The bioremovable polymer and bioremovable ceramic material may be any of the materials described in connection with the stent 10. It should also be appreciated that the bioremovable polymer layer need not include only a single polymer, but it can include mixtures of one or more bioremovable polymers.

In one embodiment, the bioremovable ceramic material may be fully dense or may be porous. For example, the bioremovable ceramic material have pore sizes from 1 nanometer to 0.1 microns. The methods for making the bioremovable ceramic material may be altered to impart the desired amount of porosity.

Figure 8:
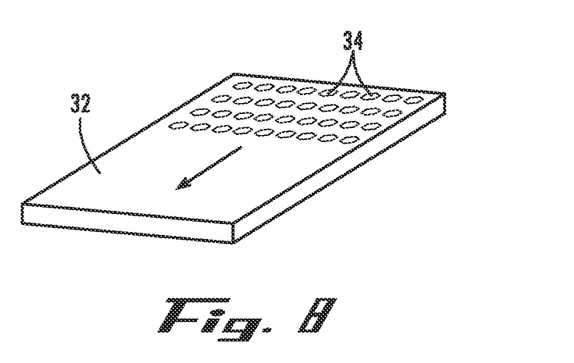
FIG. 8 shows a perspective view of the sheet of FIG. 7 as holes are being made in the sheet.
Figure 9:
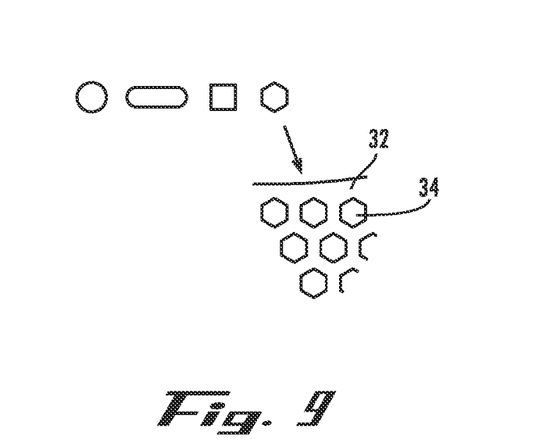
FIG. 9 shows one of a number of embodiments of the geometrical shapes that the holes in the sheet in FIG. 8 may have.

In one embodiment, the bioremovable ceramic material may be a layer of sintered flakes that are deposited on top of an underlying bioremovable polymer layer as the stent sheet 32 is built, layer by layer. These flakes may be prepared by the sol method described in connection with making ceramic fibers 16 except that instead of forming fibers, the sol, for example of tricalcium phosphate, is cast as a solution onto a plate where after drying it is broken into small pieces and screened to get uniform sized flakes. The flakes may be 1 to 10 microns thick and up to a few hundred microns wide. They may be sintered up to about 1150° C. to achieve full density or at lower temperatures to achieve a desired porosity. The polymer layers of the sheet 32 may be of the same polymers described for ceramic fibers 16. Openings in the sheet 32 may be cut as shown in FIGS. 8 and 9.

In yet another embodiment, the bioremovable ceramic layer may be a continuous sheet of, for example, sintered tricalcium phosphate on the order of 10 microns thick. It may be made using the process described in U.S. Pat. Nos. 3,436,307 and 3,444,929, both of which are hereby incorporated by reference herein in their entireties. In this process, a dispersion of submicron to micron size particles of ceramic material is dispersed with a binder in a liquid, e.g., about 10% methylcellulose in water or alternatively polyvinyl butyral in toluene or other suitable solvent. The dispersion is tape-cast onto a plastic sheet and dried. The sheet may then be sintered so as to keep it flat. Such sheets can have a thickness of about 10 to 20 microns. Sintering to achieve flat sheets may require placing alumina microspheres under and over the sheets. The particles of tricalcium phosphate in this example are expected to meet ASTM purity standards F1088-04a for use as implants. The stent sheets are then used to construct an alternating layer structure, bioremovable polymer/ceramic as described above for the flake construction. Openings in the stent sheet may be cut as in FIGS. 8 and 9.

The sheet 32 may be prepared by coating a ceramic material sheet with a solution of 0.1 grams of PLA/PGA (90/10 to 10/90) in 5 cc of a suitable solvent such as methylene chloride or acetone. Once the ceramic material sheet has been completely coated, another ceramic material sheet is positioned over the coated side of the first ceramic material sheet. The coating process may then be repeated on this new composite ceramic polymer material sheet. This process is used to provide the desired number of layers in the sheet 32.

Referring to FIG. 7, one embodiment of the sheet 32 is shown having five layers of material. More specifically, the sheet 32 includes a top layer of bioremovable polymer material 44, an intermediate layer of bioremovable polymer material 46, and a bottom layer of bioremovable polymer material 48. In between the top layer 44 and the intermediate layer 46 is a first layer of bioremovable ceramic material 50, and in between the intermediate layer 46 and the bottom layer 48 is a second layer of bioremovable ceramic material 52. It should be appreciated that the sheet 32 may have more or less than five layers. For example, the sheet 32 may have at least three layers, at least five layers, at least seven layers, or at least nine layers.

Referring to FIGS. 8 and 9, the sheet 32 may include openings 34 having any of a number of suitable shapes. For example, as shown in FIG. 9, the openings 34 may include hexagonal openings, or, in other embodiments, square, circular, oval, or other shaped openings. The openings 34 may be provided to allow the vessel tissue to still be in contact with the material moving through the vessel.

It should be appreciated that any of the stents 10, 30 described herein may also be coated with a drug eluting coating, or may incorporate a drug into the bioremovable polymer coatings or layers. Suitable drugs include, for example, heparin prostacyclin, angiopeptin, and/or methotrexate.

Illustrative Embodiments

Reference is made in the following to a number of illustrative embodiments of the subject matter described herein. The following embodiments illustrate only a few selected embodiments that may include the various features, characteristics, and advantages of the subject matter as presently described. Accordingly, the following embodiments should not be considered as being comprehensive of all of the possible embodiments. Also, features and characteristics of one embodiment may and should be interpreted to equally apply to other embodiments or be used in combination with any number of other features from the various embodiments to provide further additional embodiments, which may describe subject matter having a scope that varies (e.g., broader, etc.) from the particular embodiments explained below. Accordingly, any combination of any of the subject matter described herein is contemplated.

According to one embodiment, a composite stent comprises: a loose network of woven fibrous material configured to expand in a lumen, the fibrous material including bioremovable ceramic material; and a bioremovable polymer which coats the fibrous material. The bioremovable ceramic material may include calcium phosphate material and/or bioactive glass. The bioremovable ceramic material may include tricalcium phosphate. The bioremovable polymer may be a first bioremovable polymer and wherein the bioremovable ceramic material may be coated with the first bioremovable polymer and the first bioremovable polymer may be coated with a second bioremovable polymer. The second bioremovable polymer may have a modulus of elasticity that is lower than the first bioremovable polymer. The bioremovable polymer may have elastomeric properties such that the fibrous materials resist sliding past one another when the stent is expanded.

According to another embodiment, a composite stent comprises: a plurality of composite yarns woven together to form a network configured to expand in a lumen, each of the plurality of composite yarns including a plurality of bioremovable ceramic fibers coated with a bioremovable polymer; wherein at least substantially all of the plurality of bioremovable ceramic fibers are positioned substantially parallel to each other. The bioremovable polymer may be a first bioremovable polymer and wherein the composite stent comprises a second bioremovable polymer which forms a coating over the first bioremovable polymer. The first bioremovable polymer may provide resiliency to the composite stent and the first bioremovable polymer and/or the second bioremovable polymer may provide sufficient friction to hold the network in place upon expansion in the lumen. The first bioremovable polymer may comprise polylactide and/or polyglycolide. The bioremovable ceramic fibers may include tricalcium phosphate.

According to another embodiment, a composite stent comprises: a continuous cylindrical network of woven fibrous material configured to expand in a lumen, the fibrous material including bioremovable ceramic material; and a bioremovable polymer which coats the fibrous material.

According to another embodiment, a composite stent comprises: a network of woven fibrous material configured to expand in a lumen without substantial rotational movement of the fibrous material relative to a longitudinal axis of the composite stent, the fibrous material including bioremovable ceramic material; and a bioremovable polymer which coats the fibrous material.

According to another embodiment, a composite stent comprises: a plurality of substantially cylindrical composite yarns woven together to form a network which is configured to expand in a lumen, each of the plurality of composite yarns including a plurality of bioremovable ceramic fibers coated with a bioremovable polymer.

According to another embodiment, a composite stent comprises: a plurality of composite yarns which form a loose, woven, continuous, cylindrical network configured to expand in a lumen, each of the plurality of composite yarns including a plurality of bioremovable ceramic fibers oriented substantially parallel to each other; wherein the plurality of bioremovable ceramic fibers are coated with a first bioremovable polymer and the first bioremovable polymer is coated with a second bioremovable polymer.

According to another embodiment, a composite stent comprises: a first layer comprising bioremovable ceramic material; a second layer comprising a bioremovable polymer, the second layer being coupled to the first layer to form a sheet; wherein the sheet is coiled and configured to expand in a lumen. The bioremovable ceramic material may include calcium phosphate material and/or bioactive glass. The bioremovable ceramic material may include tricalcium phosphate. The bioremovable polymer may comprise polylactide and/or polyglycolide. The composite stent may comprise a third layer which includes bioremovable polymer, the third layer being coupled to the first layer so that the first layer is positioned between the first layer and the third layer. The composite stent may comprise a fourth layer which includes a bioremovable ceramic material and a fifth layer which includes bioremovable polymer, the fourth layer being coupled to the third layer and the fifth layer being coupled to the fourth layer so that the fourth layer is positioned between the third layer and the fifth layer. The sheet may include a plurality of openings. The openings may have any suitable geometrical shape such as hexagonal, circular, triangular, and the like. The sheet may be about 10 microns to 200 microns thick. The first layer may include a plurality of flakes of bioremovable ceramic material.

According to another embodiment, a composite stent comprises: a first layer comprising bioremovable ceramic material flakes; a second layer comprising a bioremovable polymer, the second layer being coupled to the first layer to form a sheet; wherein the sheet is wound and configured to expand in a lumen.

According to another embodiment, a composite stent comprises: a plurality of layers comprising a layer which includes a bioremovable ceramic material which is coupled to another layer which includes a bioremovable polymer; wherein the plurality of layers is wound and configured to expand in a lumen.

According to another embodiment, a composite stent comprises: a multi layer sandwich which includes a layer of bioremovable ceramic material coupled to a layer which includes a bioremovable polymer which provides resilience to the sandwich; wherein the sandwich includes plurality of holes therethrough; wherein the sandwich is configured to be wound and inserted into a lumen; and wherein the sandwich is configured to unwind and expand to a fixed position in the lumen. The layer of ceramic material may include bioremovable ceramic material.

The terms recited in the claims should be given their ordinary and customary meaning as determined by reference to relevant entries (e.g., definition of "plane" as a carpenter's tool would not be relevant to the use of the term "plane" when used to refer to an airplane, etc.) in dictionaries (e.g., consensus definitions from widely used general reference dictionaries and/or relevant technical dictionaries), commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used herein in a manner more expansive than its ordinary and customary meaning, the term should be given its ordinary and customary meaning plus the additional expansive meaning, or (b) if a term has been explicitly defined to have a different meaning by reciting the term followed by the phrase "as used herein shall mean" or similar language (e.g., "herein this term means," "as defined herein," "for the purposes of this disclosure [the term] shall mean," etc.). References to specific examples, use of "i.e.," use of the word "invention," etc., are not meant to invoke exception (b) or otherwise restrict the scope of the recited claim terms. Accordingly, the subject matter recited in the claims is not coextensive with and should not be interpreted to be coextensive with any particular embodiment, feature, or combination of features shown herein. This is true even if only a single embodiment of the particular feature or combination of features is illustrated and described herein. Thus, the appended claims should be read to be given their broadest interpretation in view of the prior art and the ordinary meaning of the claim terms.

As used herein, spatial or directional terms, such as "left," "right," "front," "back," and the like, relate to the subject matter as it is shown in the drawing FIGS. However, it is to be understood that the subject matter described herein may assume various alternative orientations and, accordingly, such terms are not to be considered as limiting. Furthermore, as used herein (i.e., in the claims and the specification), articles such as "the," "a," and "an" can connote the singular or plural. Also, as used herein, the word "or" when used without a preceding "either" (or other similar language indicating that "or" is unequivocally meant to be exclusive—e.g., only one of x or y, etc.) shall be interpreted to be inclusive (e.g., "x or y" means one or both x or y). Likewise, as used herein, the term "and/or" shall also be interpreted to be inclusive (e.g., "x and/or y" means one or both x or y). In situations where "and/or" or "or" are used as a conjunction for a group of three or more items, the group should be interpreted to include one item alone, all of the items together, or any combination or number of the items. Moreover, terms used in the specification and claims such as have, having, include, and including should be construed to be synonymous with the terms comprise and comprising.

Unless otherwise indicated, all numbers or expressions, such as those expressing dimensions, physical characteristics, etc. used in the specification are understood as modified in all instances by the term "about." At the very least, and not as an attempt to limit the application of the doctrine of equivalents to the claims, each numerical parameter recited in the specification or claims which is modified by the term "about" should at least be construed in light of the number of recited significant digits and by applying ordinary rounding techniques. Moreover, all ranges disclosed herein are to be understood to encompass any and all subranges subsumed therein. For example, a stated range of 1 to 10 should be considered to include any and all subranges between and inclusive of the minimum value of 1 and the maximum value of 10; that is, all subranges beginning with a minimum value of 1 or more and ending with a maximum value of 10 or less (e.g., 5.5 to 10).

What is claimed is:

1. A composite stent comprising:
    at least two layers each of which comprises a plurality of flakes of bioremovable ceramic material, each one of the plurality of flakes having a thin, flat shape; and
    at least three layers each of which comprises bioremovable polymer, the at least two layers that comprise bioremovable ceramic material being coupled to the at least three layers that comprise bioremovable polymer to form a sheet;
    wherein the stent is configured so that each of the at least two layers that comprise bioremovable ceramic material is positioned between two of the at least three layers that comprise bioremovable polymer; and
    wherein the sheet is coiled and configured to expand in a lumen.

2. The composite stent of claim 1 wherein the plurality of flakes of bioremovable ceramic material in each of the at least two layers are coupled together.

3. The composite stent of claim 1 wherein the bioremovable ceramic material includes calcium phosphate material and/or bioactive glass.

4. The composite stent of claim 3 wherein the bioremovable ceramic material includes tricalcium phosphate.

5. The composite stent of claim 1 wherein the bioremovable polymer comprises polylactide and/or polyglycolide.

6. The composite stent of claim 1 wherein there are at least three of the layers that comprise a plurality of flakes of bioremovable ceramic material and there are at least four of the layers that comprise bioremovable polymer, and wherein the stent is configured so that each one of the at least three layers that comprise bioremovable ceramic material is alternatively positioned between two of the at least four layers that comprise bioremovable polymer.

7. The composite stent of claim 6 wherein there are at least four of the layers that comprise a plurality of flakes of bioremovable ceramic material and there are at least five of the layers that comprise bioremovable polymer, and wherein the stent is configured so that each one of the at least four layers that comprise bioremovable ceramic material is alternatively positioned between two of the at least five layers that comprise bioremovable polymer.

8. The composite stent of claim 1 wherein the sheet includes a plurality of openings.

9. The composite stent of claim 8 wherein the openings have a hexagonal shape.

10. The composite stent of claim 1 wherein the sheet is about 10 microns to 200 microns thick.

11. The composite stent of claim 1 wherein the plurality of flakes are embedded in bioremovable polymer.

12. A composite stent comprising:
a first layer which includes a plurality of flakes of bioremovable ceramic material, each one of the plurality of flakes having a thin, flat shape; and
a second layer and a third layer each of which comprises bioremovable polymer;
wherein the first layer is positioned between the second layer and the third layer.

13. The composite stent of claim 12 wherein the bioremovable ceramic material includes calcium phosphate material and/or bioactive glass.

14. The composite stent of claim 12 wherein the bioremovable ceramic material includes tricalcium phosphate.

15. The composite stent of claim 12 wherein the bioremovable polymer comprises polylactide and/or polyglycolide.

16. The composite stent of claim 12 comprising a fourth layer which includes bioremovable ceramic material and a fifth layer which includes bioremovable polymer, the fourth layer being coupled to the third layer and the fifth layer being coupled to the fourth layer so that the fourth layer is positioned between the third layer and the fifth layer.

17. The composite stent of claim 12 wherein the bioremovable ceramic material is porous.

18. The composite stent of claim 12 wherein the first layer, the second layer, and the third layer form at least part of a sheet that is about 10 microns to 200 microns thick.

19. The composite stent of claim 12 wherein the first layer, the second layer, and the third layer form at least part of a sheet that is coiled and configured to expand in a lumen.

20. The composite stent of claim 12 wherein the plurality of flakes are embedded in bioremovable polymer.

21. A composite stent comprising: a first layer including bioremovable ceramic material; a second layer including bioremovable polymer, the second layer being coupled to the first layer; a third layer including bioremovable polymer, the third layer being coupled to the first layer so that the first layer is positioned between the second layer and the third layer; a fourth layer which includes bioremovable ceramic material, the fourth layer being coupled to the third layer; and a fifth layer which includes bioremovable polymer, the fifth layer being coupled to the fourth layer so that the fourth layer is positioned between the third layer and the fifth layer.

22. The composite stent of claim 21 wherein the bioremovable ceramic material in the first layer and the fourth layer includes tricalcium phosphate.

23. The composite stent of claim 21 wherein the bioremovable polymer in the second layer, the third layer, and the fifth layer includes polylactide and/or polyglycolide.

24. The composite stent of claim 21 wherein the bioremovable ceramic material in the first layer and the fourth layer is porous.

25. The composite stent of claim 21 wherein the stent is configured to move between a contracted configuration where the stent is sized to be maneuvered through a bodily lumen and an expanded configuration where the stent is in contact with the interior of the bodily lumen to facilitate the flow of fluid through the bodily lumen.

26. A composite stent comprising a layer that includes a plurality of flakes of bioremovable ceramic material, each one of the plurality of flakes having a thin, flat shape.

27. The composite stent of claim 26 comprising bioremovable polymer.

28. The composite stent of claim 26 wherein the bioremovable ceramic material includes tricalcium phosphate.

29. The composite stent of claim 26 wherein the plurality of flakes are embedded in bioremovable polymer.

30. A composite stent comprising alternating layers of bioremovable ceramic material and bioremovable polymer, wherein the stent includes at least two layers of bioremovable ceramic material and the stent is expandable.

31. The composite stent of claim 30 comprising at least three layers of bioremovable polymer.

32. The composite stent of claim 30 wherein each of the at least two layers of bioremovable ceramic material is made up of a plurality of flakes of bioremovable ceramic material, each one of the plurality of flakes having a thin, flat shape.

33. The composite stent of claim 30 wherein the bioremovable ceramic material is porous.

34. The composite stent of claim 30 wherein the bioremovable polymer comprises polylactide and/or polyglycolide.

35. The composite stent of claim 30 wherein an outermost layer of the composite stent is one of the layers of bioremovable polymer.

* * * * *